United States Patent [19]
Shouts

[11] Patent Number: 5,919,192
[45] Date of Patent: Jul. 6, 1999

[54] COMPRESSION-DISTRACTION APPARATUS FOR TREATMENT OF A BONE FRACTURE

[75] Inventor: Semen Shouts, Haifa, Israel

[73] Assignee: Cottec Orthopaedic Technologies Development Ltd., Haifa, Israel

[21] Appl. No.: 08/872,425

[22] Filed: Jun. 10, 1997

[51] Int. Cl.[6] .................................................. A61B 17/56
[52] U.S. Cl. ............................... 606/56; 606/57; 606/58; 606/59; 606/102
[58] Field of Search ................................. 606/56, 57, 58, 606/59, 102

[56] References Cited

U.S. PATENT DOCUMENTS

| | | | |
|---|---|---|---|
| 5,728,095 | 3/1998 | Taylor et al. ............................... | 606/56 |
| 5,738,684 | 4/1998 | Thomas et al. ............................. | 606/57 |

FOREIGN PATENT DOCUMENTS

| | | | |
|---|---|---|---|
| 971294 | 11/1982 | Russian Federation . | |
| 1277959 | 12/1986 | Russian Federation . | |
| 438413 | 8/1974 | U.S.S.R. ................................. | 606/102 |

*Primary Examiner*—Michael Buiz
*Assistant Examiner*—Julian W. Woo
*Attorney, Agent, or Firm*—Frishauf, Holtz, Goodman, Langer & Chick

[57] ABSTRACT

A compression-distraction apparatus for fixation of two fragments of a fractured bone comprises three annular members placed in spaced-apart alignment around the limb of the broken bone. It features two outer members are each connected to one of the fragments by at least two through-going pins, while a third, median member is connected to the outer members by three bolts or studs after proper alignment of the fragments. A first outer member is to connected to the median member in non-parallel manner by bolts having a pivot incorporated therein, while firm connection to the second outer member is made only after measurement of the compression or distraction forces. For this purpose three gauges in the form of bent leaf springs and sensors are mounted between the median and the second member for measuring the force exerted by the placement of the first outer member in regard to the median member, and the second member is firmly secured to the median member by the aforementioned three bolts or studs only after attainment of a predesignated force.

9 Claims, 8 Drawing Sheets

COMPRESSION-DISTRACTION APPARATUS FOR TREATMENT OF A BONE FRACTURE

The invention relates to a medical instrument for the connection of a fractured bone in an upper or lower extremity. It relates particularly to an apparatus fitted externally to the limb and is adapted to keep the bone fragments in position and/or under compression or distraction. The apparatus is furthermore configured to change the angular alignment of the fractured bone fragments in contradistinction to the existing apparatus which keep the fractured parts in straight alignment only.

BACKGROUND OF THE INVENTION

A fractured bone is either connected by an intermedullary nail or by a compression-distraction apparatus in the form of annular members which are mounted around the limb and are connected to the bone fragments by long pins extending through tissue and bone, preferably in crossed alignment, and have their ends firmly connected to the annular members. The latter are interconnected by screws or studs which allow changing their distance from each other in order to shorten or to lengthen the bone.

A typical apparatus is disclosed in SU 971294 which includes two assemblies each containing two rings rigidly connected in spaced relationship by screws and adapted to secure one bone fragment by cross-wise extending pins rigidly connecting the bone to the respective assembly. The two aseemblies are interconnected by spring-loaded screws which effect traction or compression on the fracture in accordance with necessity. The apparatus suffers ffrom the drawback that it provides no means for accurate measuring of the distraction or compression force applied to the fractured bone, and that it provides no means for adjusting the angular alignment of the bone portions with the aim to restore the bone's original shape and curvature.

A second typical apparatus is disclosed in SU 1277959 which includes two outer ring-shaped members surrounding the limb and holding the two fractured bone parts by cross-wise extending pins, and an intermediate ring-shaped member which is not connected to any bone part. The intermediate member is rigidly connected to one of the outer members by screws which permit changing the distance between the two members in accordance with the force to be applied. The intermediate member and the second outer member are not rigidly connected by held in their relative position by three U-shaped springs which have their one end connected to the outer member and are supported on the intermediate member by one steel ball each. Pressure acting on the springs is indicated by annular sensors inside the "U". The main drawback of this apparatus is the impossibility to adjust the angle between the bone fragments, besides the fact that force measurements by means of the annular sensors are very inaccurate. A third drawback is that the components have to be changed for compression and distraction purposes respectively. Still another drawback is the fact that the applied force and change of length have to be continuously read during the entire period of adjustment.

It is the main object of the present invention to avoid these drawbacks and to provide a medical apparatus that will be suitable in promoting rapid and exact healing of a bone fracture in an upper or lower extremity.

It is a second object of the invention to provide an apparatus which will permit application of accurate predesignated tension or pressure force onto the fracture by means of accurate measuring devices.

It is another object to provide means for quick and accurate reading of the forces and length adjustment of the apparatus while it is mounted on the fracture.

It is another object to provide an apparatus which will permit adjustment and possible changing of the angular alignment of the bone fragments so as to restore the original shape of the bone during healing.

Another object is to provide an apparatus which will enable the surgeon to meassure the stiffness of the fracture as well as the angular alignment of the fragments during all stages of healing.

SUMMARY OF THE INVENTION

The medical apparatus for compression or distraction of a bone fracture according to the present invention includes essentially two outer annular members and an intermediate annular member, all of similar dimensions and of an inner diameter somewhat larger than the size of the upper or lower extremity enclosing the fractured bone. Each of the outer members is configured to secure one bone fragment by at least two long pins extending through the bone and the limb tissue and have their two ends firmly connected to the member. The intermediate member is not connected to either bone or limb, but is adjustably connected to one of the outer members by studs or bolts which permit changing or their relative distance by adjustment of the nuts along the screw thread with the object of applying compression or distraction on the fracture. In addition non-parallel alignment of the two members can be obtained by fastening the studs or bolts to the intermediate member by a ball-joint which permits their angular displacement. The second outer member is connected to the intermediate member by several bolts or studs which keep the two members at a substantially constant distance. The two members are further connected by several—preferably three—stress gauges in the form of C-shaped leaf-springs each carrying a sensor attached to its back which is electrically connected to an electronic processor. Each sensor is actuated by the curvature of the spring to emit appropriate signals to be transmitted to the processor which is adapted to convert these signals into a digital pressure indication.

The distance between the two outer members can be measured in different ways. In a preferred embodiment of the invention they are connected by a flexible wire which has its one end attached to an electronic measuring device of known design which is adapted to emit signals to a distance indicating processor.

A second embodiment of the apparatus permitting greater flexibility of the three annular members is characterized by the provision of hinges in the bolts or studs connecting the intermediate member with one of the outer members and by means of changing the distance between the intermediate member and both outer annular members. It is further characterized by greater accuracy in stress measurement by providing frame-shaped leaf-springs which are connected to the respective annular members so as to prevent lateral forces from influencing the measurement results.

DETAILED DESCRIPTION OF THE DRAWINGS

Figure 1:
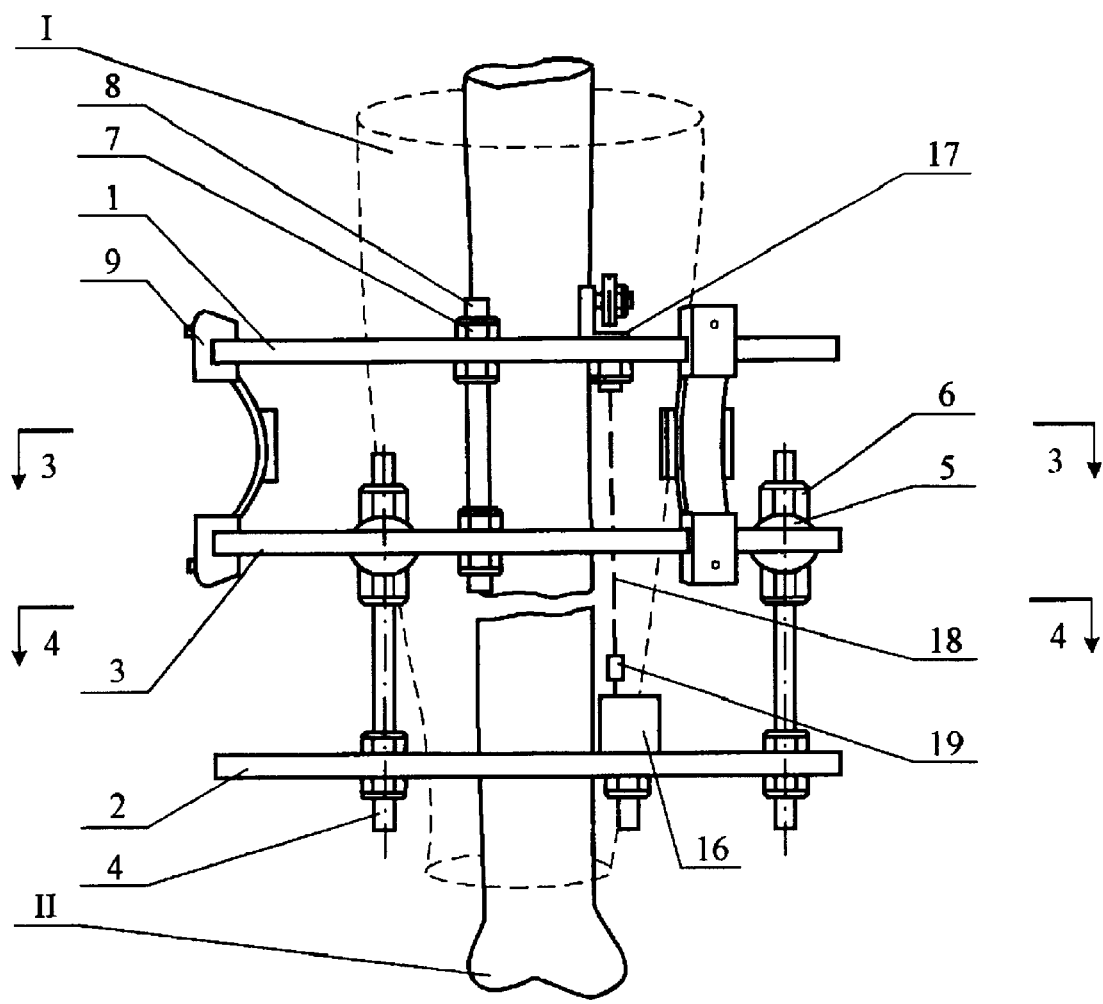
FIG. 1 is a side view of the apparatus of the invention.

Referring now to FIGS. 1 through 6 of the drawings the apparatus for the above described purpose includes two outer annular members 1 and 2 and an intermediate annular member 3 which are of substantially identical shape and have an inner diameter somewhat larger than that of the limb I enclosing the fractured bone II. In the following description reference will be made to the position of the apparatus as appearing in the drawing and the expressions "top" and "bottom" and "upper" and "lower" will be used, but it will be understood that in actual use the apparatus can be mounted on the limb in any direction. Two pairs of long pins III extend through the two bone fragments and the limb tissue and have their respective ends fastened to the upper and lower member. The intermediate and the lower member are firmly inter-connected by three studs 4 and nuts 6 whereby the upper stud ends are held in ball joints 5 shown in detail in FIG. 5. The ball joint connection permits positioning of the two members not in co-axial alignment, i.e. with the axes of the two bone fragments meeting at an angle. The upper annular member 1 is connected to the intermediate member by three studs 8 and nuts 7 and by three stress gauges 9 (FIG. 6) each composed of a C-shaped leaf spring 11 and a sensor 12 which is attached to the back of the "C" and is configured to sense the changes in the curvature of the spring with changing force applied to it and to emit appropriate electrical signals to a processing unit. The ends of each spring are firmly attached to clamps 13 which connect it to points on the upper and intermediate member by means of wedges 14. As visible in FIG. 6 the wedges are pulled into the space between clamp and member by screws 15 clamping the spring firmly into position. In this connection is should be mentioned that this manner of attaching the spring ends to the members represents only one embodiment, and that many other connection modes may be used instead. In the present drawing three studs 8 and three stress gauges are shown to connect the two members, but it will be understood that there is the possibility to install more, as for instance four of each component.

Figure 5:
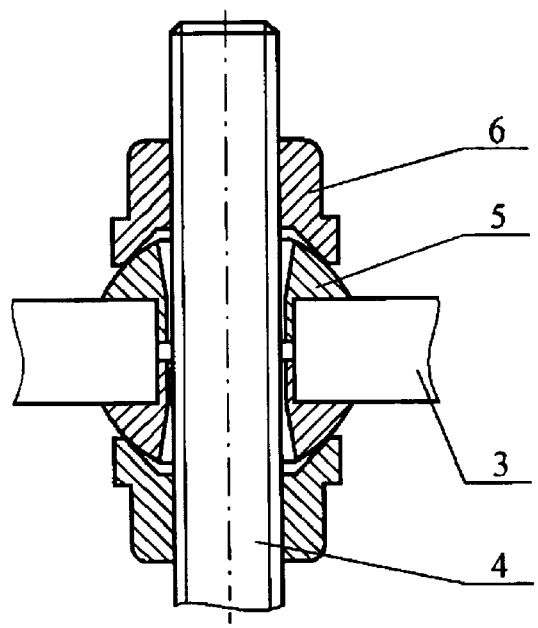
FIG. 5 is a section of the ball-joint connection of a bolt in the intermediate member.
Figure 6:
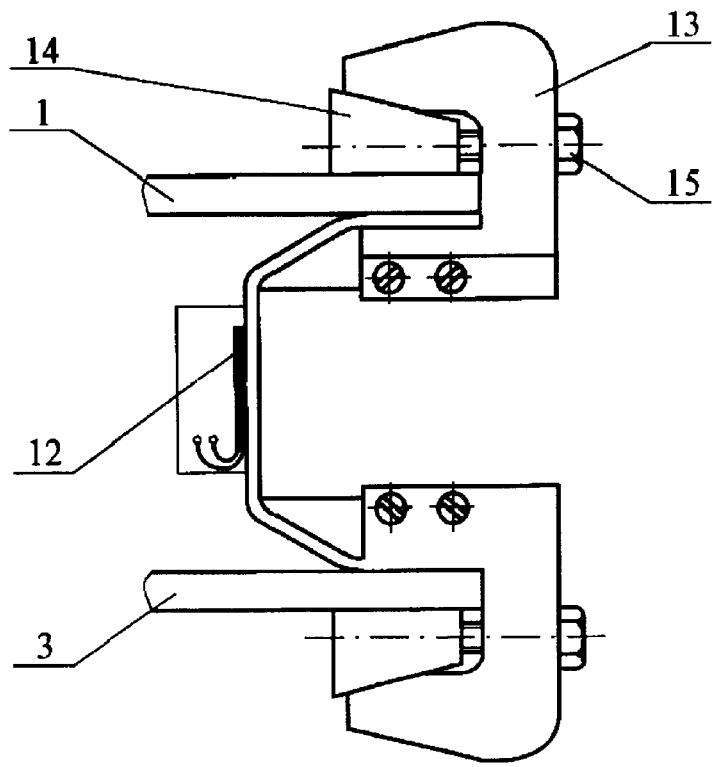
FIG. 6 is a side view of one of the stress gauges and their connection to two annular members.

The ball-joint connection of stud 4 to the intermediate member is shown in detail in FIG. 5. Herein two hemispherical members 5 are fastened in the two sides of a bore extending through member 3 and permit a limited angular movement of stud 4 in conical bores 5'. The nuts 6 are provided with hemispherical recesses conforming to the shape of the hemispherical members in order to firmly secure the stud in its position.

Figure 7:
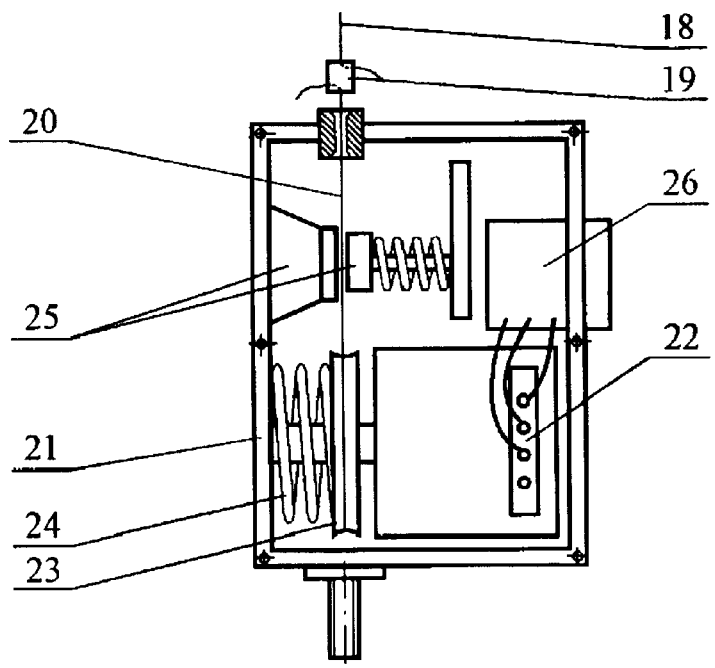
FIG. 7 illustrates the distance measuring device, with the cover removed.

The relative displacement of the outer members 1 and 2 can be measured by various means, as for instance by means of a tape-measure, but automatic measuring and recording may be preferable because of the accuracy in obtaining results. An embodiment of a measuring device is illustrated in FIGS. 1 and 7 showing a flexible wire 18 stretched between the two outer members. It is fastened to the upper member 1 by means of a bobbin 17 which permits its lengthening or shortening in accordance with the distance of the two annular members and to the lower member 2 by the sensor 16 enclosed in a casing 21. The sensor includes a flexible wire 20 releasably connected to wire 18 by a coupling 19. Wire 20 extends through a spring-operated brake 25 to a pulley 23 on which it is wound up by means of a rotary spring 24. The pulley is connected to a potentiometer 22 which indicates the position of pulley 23 by electrical signals transmitted to a processing unit through a connector 26 and via releasable cable means.

Figure 8:
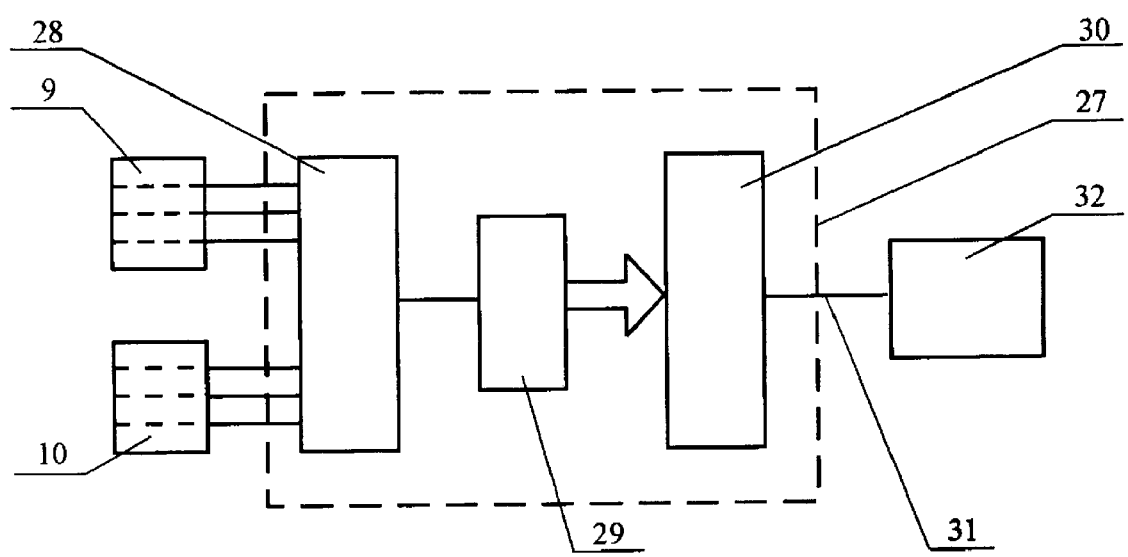
FIG. 8 is a diagram of the electronic apparatus for converting the signals issued by the stress gauges and the distance measuring device.

The processing unit is diagrammatically shown in FIG. 8; The diagram shows the stress gauge 9 and the displacement sensor 10 connected by wiring to an amplifier multiplexer block 28 which transmits the signals received from the sensors to an analog-digital converter 29, and from there through a micro-processor to a display 32.

Figure 2:
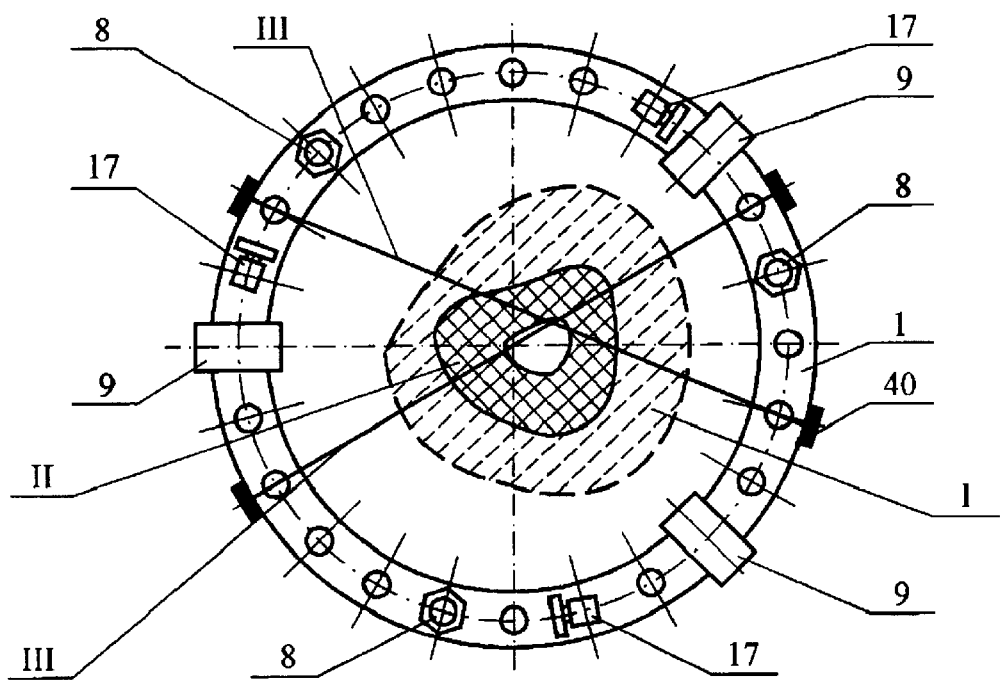
FIG. 2 is a top view of the apparatus shown in FIG. 1.
Figure 3:
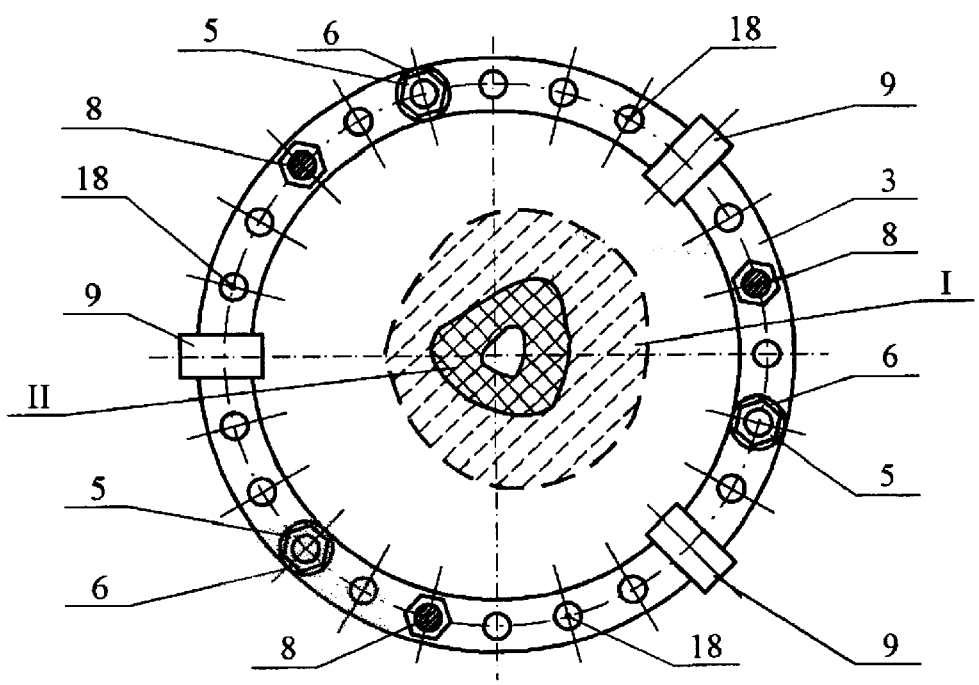
FIG. 3 is a section of the apparatus of FIG. 1 along line 3—3.
Figure 4:
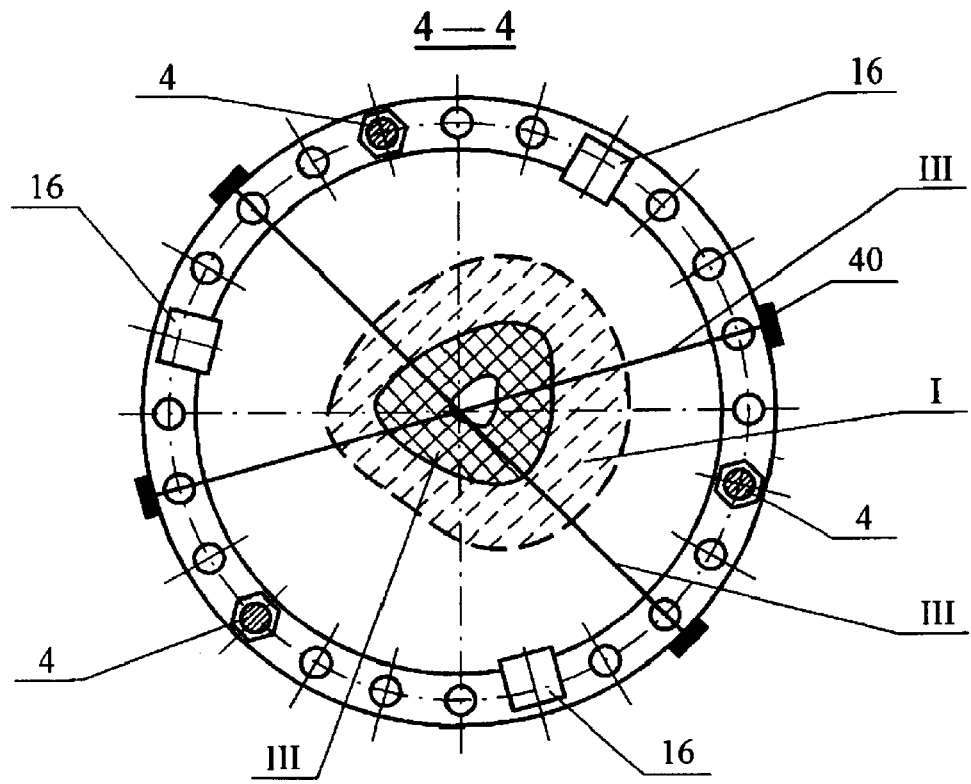
FIG. 4 is a section of the apparatus of FIG. 1 along line 4—4.

Connection of a fractured bone by means of the present apparatus is as follows: After drilling through bone and limb two long pins III are inserted into each bone fragment either crosswise or in angular alignment as shown in FIGS. 2 and 4. Now the three annular members are slipped over the limb and the pins III are connected to the outer members 1 and 2 with their ends held in rigid alignment by nuts 40. The intermediate member 2 is connected to outer member 3 by studs 4 and nuts 6, and to outer member 1 by studs 8 and nuts 7. Now the stress gauges 9 are fastened to annular members 1 and 3 by means of clamps 13 and wedges 14, whereupon the rigid connection between the three members is released by loosening the respective nuts on studs 4 and 8. This action leaves members 1 and 3 resiliently connected by springs 11, while the distance between the two bone fragments is now adjusted by adjusting the distance between members 2 and 3 with the aid of nuts 6 moved along the screw thread of studs 4. This adjustment also enables the surgeon to adjust the angular alignment of the two fragments as viewed by X-Ray imaging. The stress gauges are now connected to the processor which indicates the compression or distraction forces applied to the bone and permits the surgeon to adjust the distance between annular members 2 and 3 until the desired force is indicated. Thereafter the annular members are again connected in rigid form and the displacement sensor 16 and wire 18 are placed and connected to the outer members. The apparatus permits frequent inspection of the fracture and changing of the forces applied to the bone fragments in the manner described herein before. Changing of the distance between the outer members—and of the bone fragments—can be continuously controlled by displacement of sensor 16 and the processor shown in FIG. 8. After complete healing of the fracture as shown by X-ray imaging the instrument as well as the pins are removed.

Figure 9:
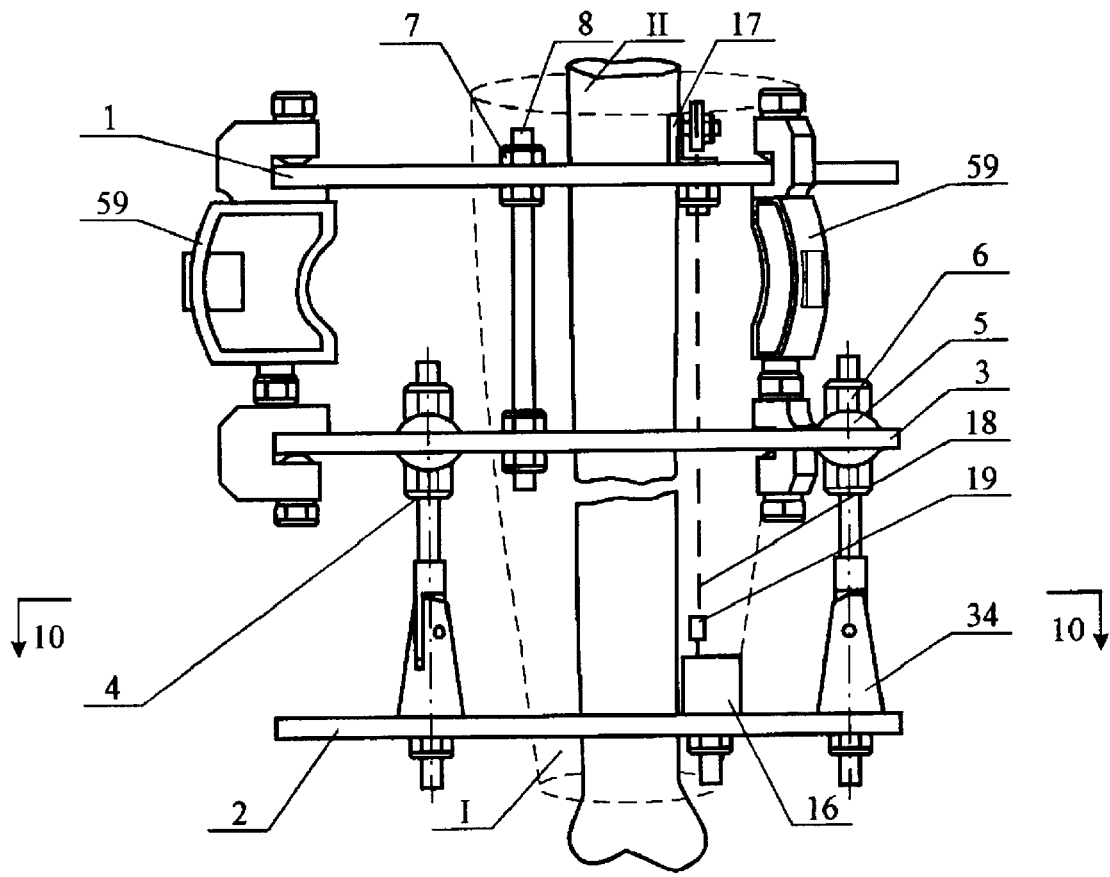
FIG. 9 is a side view of a second embodiment of the apparatus.
Figure 10:
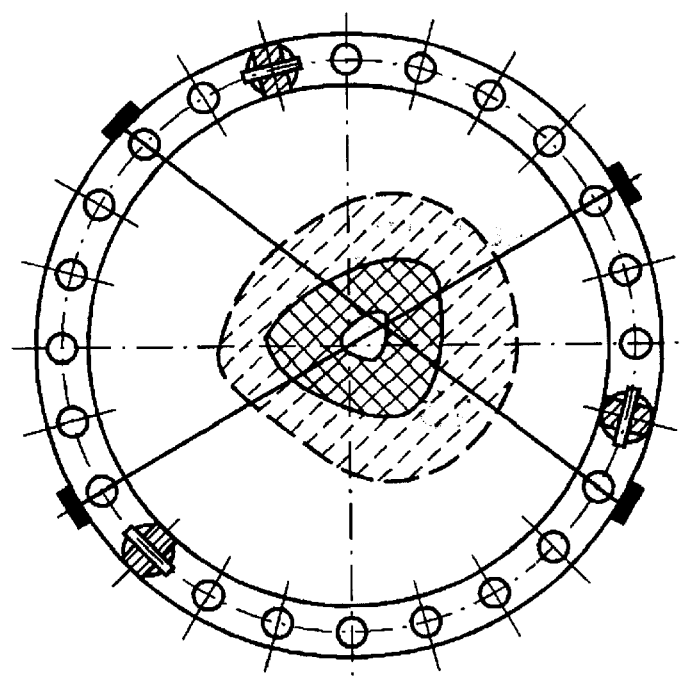
FIG. 10 is a section along line 10—10 of FIG. 9.

An improved embodiment of the apparatus as compared with that illustrated in FIG. 1 is shown in FIGS. 9 and 10. Herein the C-shaped leaf springs (9) are replaced by frame shaped springs 59 with both their parallel sides bent into C-shape, while being connected to the respective outer and intermediate member by clamps permitting certain angular movement relative to the annular members. This arrangement will be described in the following with reference to FIGS. 12A and 12B. The other feature shown in FIG. 9 is the hinged connection of the bolts 4 to annular member 2 which is shown in detail in FIGS. 11A and 11B.

Figure 12A:
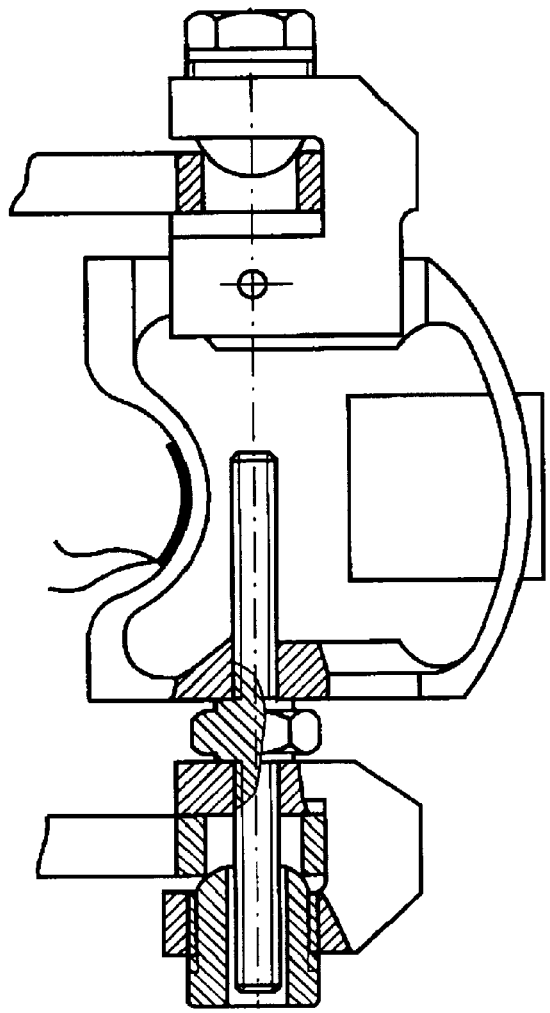
FIG. 12A is a side view of the stress gauge shown in FIG. 9.

Referring now to FIGS. 12A and B, the pressure gauges are in the shape of frame-shaped leaf springs 59 which include two straight sides substantially parallel to the planes of the annular members 1 and 3, and two sides connecting the parallel sides which are both bent into a C-shape. Sensors 12 are connected to the outer C-shaped sides, which sense the changing curvature of the springs in accordance with the force acting thereon and transmit corresponding signals to a processing unit by way of a connector 42 and wiring which is not shown in the drawing. The springs are attached to the outer annular member 1 by clamps 38 and to the intermediate member by clamps 40. In order to provide additional flexibility clamp 38 holds the spring by means of a pin 39 and is itself fastened to the member by means of a screw 41 which urges a hemispherical member 44 onto the edge of a perforation 45. In this manner the semi-cylindrical portion 48 of the clamp is urged onto the underside of the annular member thereby permitting small angular displacement of the clamp—and of the spring—in relation to the plane of the annular member.

The connection to the intermediate member 3 is by means of a clamp 40 which is fastened to the member in a similar manner as lamp 38, viz. by means of a hemispherical member 49 and a semi-cylindrical portion 50 on the clamp urged onto a perforation in member 3. Member 49 is in the shape of a screw-threaded bushing which terminates in a nut 49' serving to urge the hemisphere onto the member 3. A screw 51 holds the spring in position by extending through a screw-threaded bore in the spring and permits changing the distancce between the two annular members by rotation of hexagon 51'. In all other respects the stress gauge is operated as in the aforedescribed embodiment.

Figure 11A:
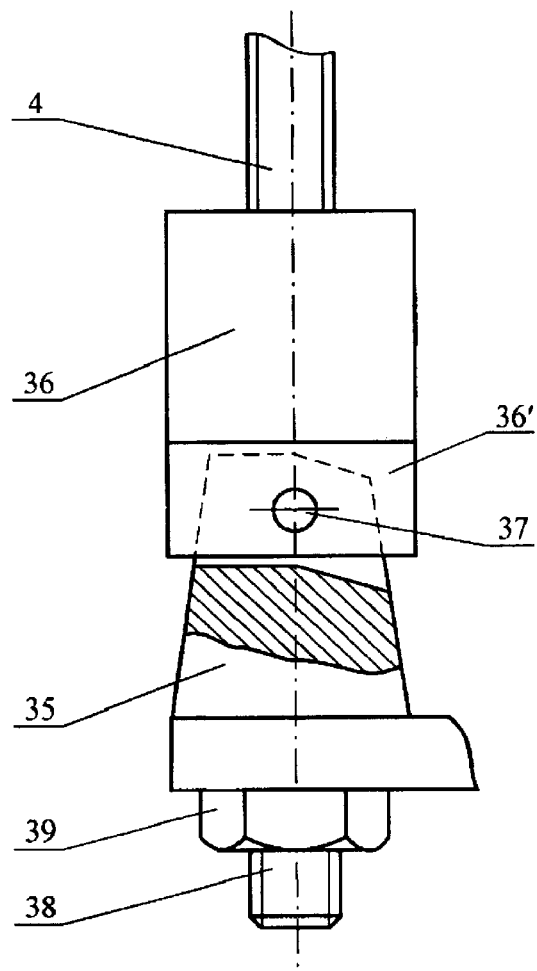
FIG. 11A is a side view of the linkage element connecting the bolts or studs to an outer member.
Figure 11B:
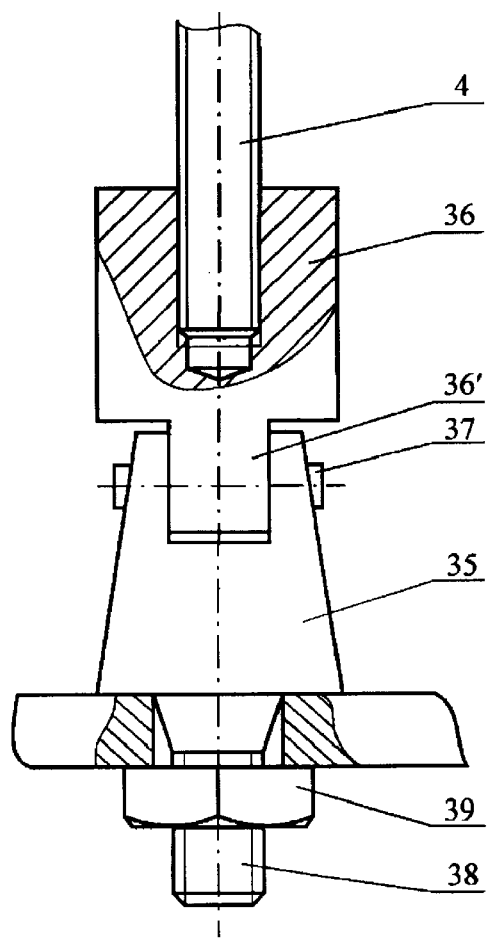
FIG. 11B is a side view of the linkage element ilustrated in FIG. 11A.
Figure 12B:
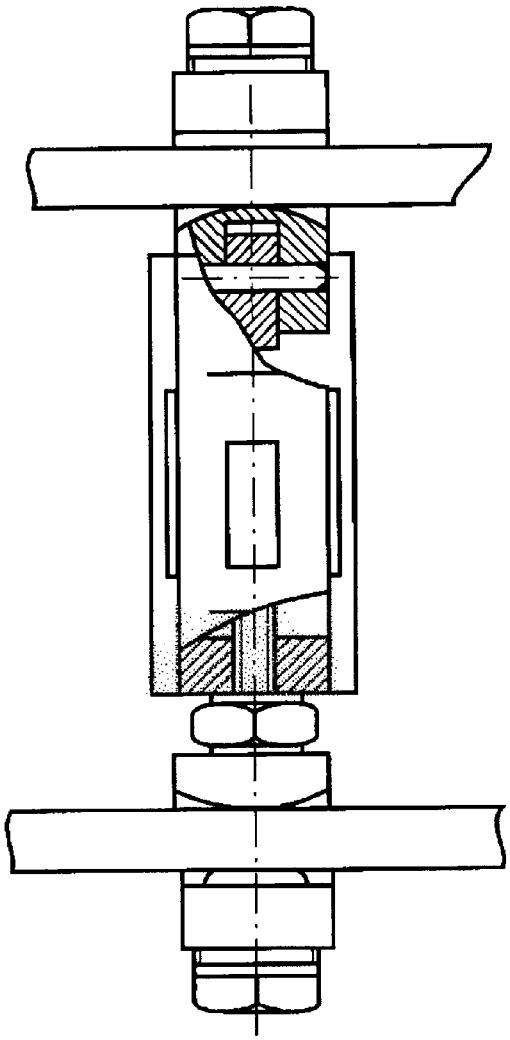
FIG. 12B is a view along line 12—12 of FIG. 12A.

Connection between annular members 2 and 3 is by means of bolts 4 which are of much shorter length than in the afore-described embodiment, but are completed by a hinge assembly illustrated in FIGS. 11A and 11B. The assembly includes an upper block 36 which is centrally threaded for reception of the end of bolt 4 and which forms a tongue 36' engaging with a recess in a lower block 35, allowing relative angular displacement by means of a pin 37 extending through tongue and recess. Block 36 is rigidly fastened to member 3 by means of screw 38 and nut 39 fastening the assembly in a manner so as to permit angular displacement towards the center of the apparatus.

The object of this hinge assembly is to prevent bending of the bolts 4 in the apparatus of FIG. 1 while the annular members 2 and 3 are brought into non-parallel alignment in order to align the bone fragments in their original position.

In all other respects the use of the original and the improved apparatus for keeping the bone fragments in their correct position during the healing process is identical in both cases, but the advantage of the latter is the prevention of material stresses and improved adjustment of the forces to be applied to the body of the patient.

I claim:

1. An apparatus for healing a bone fracture in a limb by connecting two bone fragments and applying one of compression and distraction, comprising:

a first outer annular member arranged to surround said limb and to be connected to a first fragment of said two bone fragments by a first set of at least two long pins extending through said first fragment and through a tissue portion of said limb with ends of said first set of pins firmly connected to said first annular member, a second outer annular member arranged to surround said limb and to be connected to a second fragment of said two bone fragments by a second set of at least two long pins extending through said second fragment and through said tissue portion of said limb with ends of said second set of pins firmly connected to said second annular member, an intermediate annular member arranged to surround said limb and to be positioned in spaced-apart alignment between said first and second outer annular members, a first set of at least one of three bolts and three studs connecting said first outer annular member to said intermediate annular member at a predesignated distance, at least three stress gauges connecting said first outer annular member to said intermediate annular member, each said stress gauge including: (i) a C-shaped leaf spring connecting said first outer annular member to said intermediate member with a first end of said C-shaped leaf spring rigidly connected to said first outer annular member and a second end of said C-shaped leaf spring rigidly connected to said intermediate annular member, and (ii) a sensor attached to a rear portion of said C-shaped leaf spring and configured to emit signals coordinated to a curvature of said C-shaped leaf spring as caused by varying forces acting between said first outer annular member and said intermediate annular member, a second set of at least one of three bolts and three studs connecting said second outer annular member to said intermediate member at a distance which is made variable by means of nuts movable along a screw thread provided on said second set of at least one of three bolts and three studs in order to apply one of a predesignated compression and distraction force to said bone fracture, and a processing unit configured to receive the signals emitted by said sensor of each of said at least three stress gauges, and to display the force acting on said bone fracture.

2. The apparatus of claim 1, wherein said second set of at least one of three bolts and three studs connecting said second outer annular member to said intermediate annular member are attached to said intermediate annular member by ball joints which permit angular alignment of axes of said bone fragments by varying an alignment of said second outer annular member and said intermediate annular member.

3. The apparatus of claim 1, wherein said first and second ends of said C-shaped leaf spring of each of said at least three stress gauges are respectively connected to said first outer annular member and said intermediate annular member by one clamp each.

4. The apparatus of claim 1, wherein a displacement meter is provided and conductively connected to a processor configured to display a distance between said first and second outer annular members.

5. The apparatus of claim 4, wherein said displacement meter includes a displacement sensor mounted on one of said first and second outer annular members and is connected to said second outer annular member by a flexible wire.

6. The apparatus of claim 5, wherein one end of said flexible wire is wound on a pulley which is rotated by changing a length of said flexible wire in accordance with the distance between said first and second outer annular members, said pulley being connected to a potentiometer configured to transmit signals to said processing unit in accordance with a position of said pulley.

7. The apparatus of claim 1, wherein said leaf spring comprises a portion of a frame-shaped spring including two first opposite sides substantially parallel to said first outer annular member and said intermediate annular member, respectively, and two second opposite sides arranged in a C-shaped configuration.

8. The apparatus of claim 7, wherein said frame-shaped spring is attached to a clamp connecting said frame-shaped spring to said intermediate annular member by means of a bolt permitting changing of the predesignated distance between said first outer annular member and said intermediate annular member.

9. The apparatus of claim 2, wherein a first block is secured to ends of said second set of at least one of three bolts and three studs, and a second block is connected to said second outer annular member, said first and second blocks being pivotally interconnected.

* * * * *